United States Patent [19]

Lock

[11] 4,016,870
[45] Apr. 12, 1977

[54] ELECTRONIC ACUPUNCTURE POINT FINDER

[76] Inventor: Chuck Lock, 144 - 6th Ave., San Francisco, Calif. 94118

[22] Filed: Oct. 14, 1975

[21] Appl. No.: 622,050

[52] U.S. Cl. .......................................... 128/2.1 C
[51] Int. Cl.² ................... A61B 5/05; A61H 39/02
[58] Field of Search ........... 128/2.1 C, 2.1 R, 2.1 Z

[56] References Cited

UNITED STATES PATENTS

| 3,207,151 | 9/1965 | Takagi | 128/2.1 C |
|---|---|---|---|
| 3,802,419 | 4/1974 | Yates | 128/2.1 Z |
| 3,841,316 | 10/1974 | Meyer | 128/2.1 Z |
| 3,866,600 | 2/1975 | Rey | 128/2.1 R |
| 3,894,532 | 7/1975 | Morey | 128/2.1 C |
| 3,900,020 | 8/1975 | Lock | 128/2.1 C |
| 3,924,609 | 12/1975 | Freidenberg et al. | 128/2.1 Z |

FOREIGN PATENTS OR APPLICATIONS

| 1,133,442 | 5/1955 | France | 128/2.1 C |
|---|---|---|---|
| 1,139,287 | 8/1955 | France | 128/2.1 C |
| 1,342,761 | 10/1963 | France | 128/2.1 R |
| 1,126,634 | 9/1968 | United Kingdom | 128/2.1 R |
| 997,670 | 7/1965 | United Kingdom | 128/2.1 R |

Primary Examiner—Robert W. Michell
Assistant Examiner—Lee S. Cohen
Attorney, Agent, or Firm—Bruce & McCoy

[57] ABSTRACT

An electronic acupuncture point finder comprised of a point finder electrode for passing over a patient's skin, a grabber electrode formed to be secured to or held by the patient, and a balancing and sensitivity adjustment circuit electrically connected to said point finder and grabber electrodes so as to produce an imbalance signal when the point finder electrode passes over an acupuncture point. An amplifier circuit is provided in connection with the balancing and sensitivity adjustment circuits such that the amplifier is only turned on when the body impedance is below a preselected level whereupon the amplifier circuit generates an amplified signal for driving audio and visual indicating circuits. A single d.c. voltage supply is provided for powering all circuits 4 Claims, 3 Drawing Figures

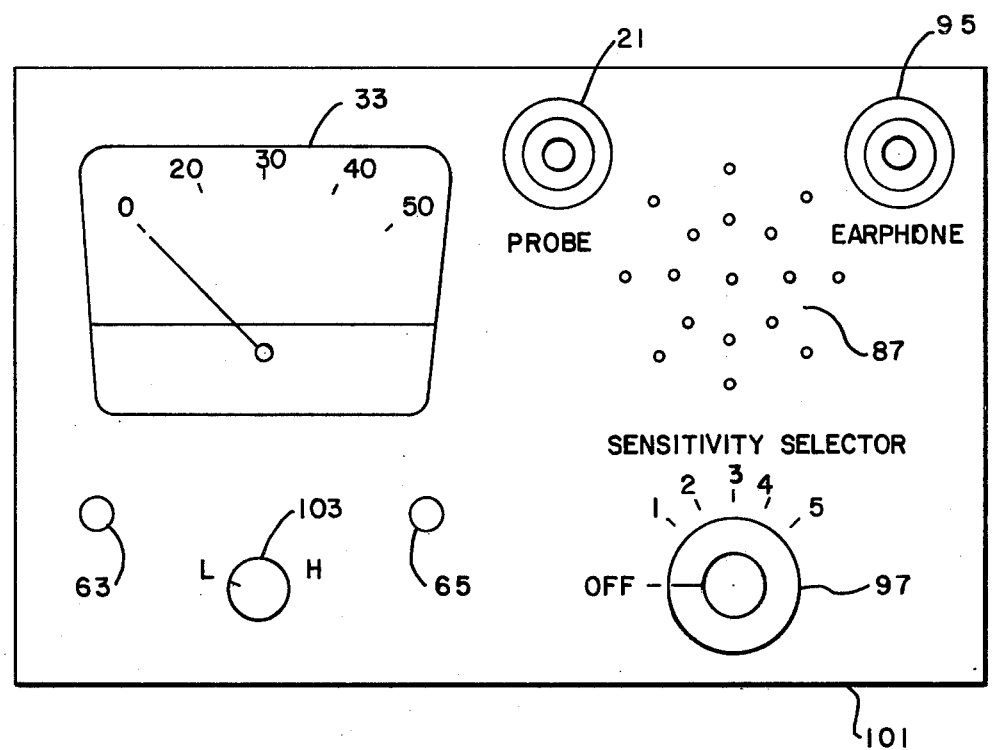
FIG.—1
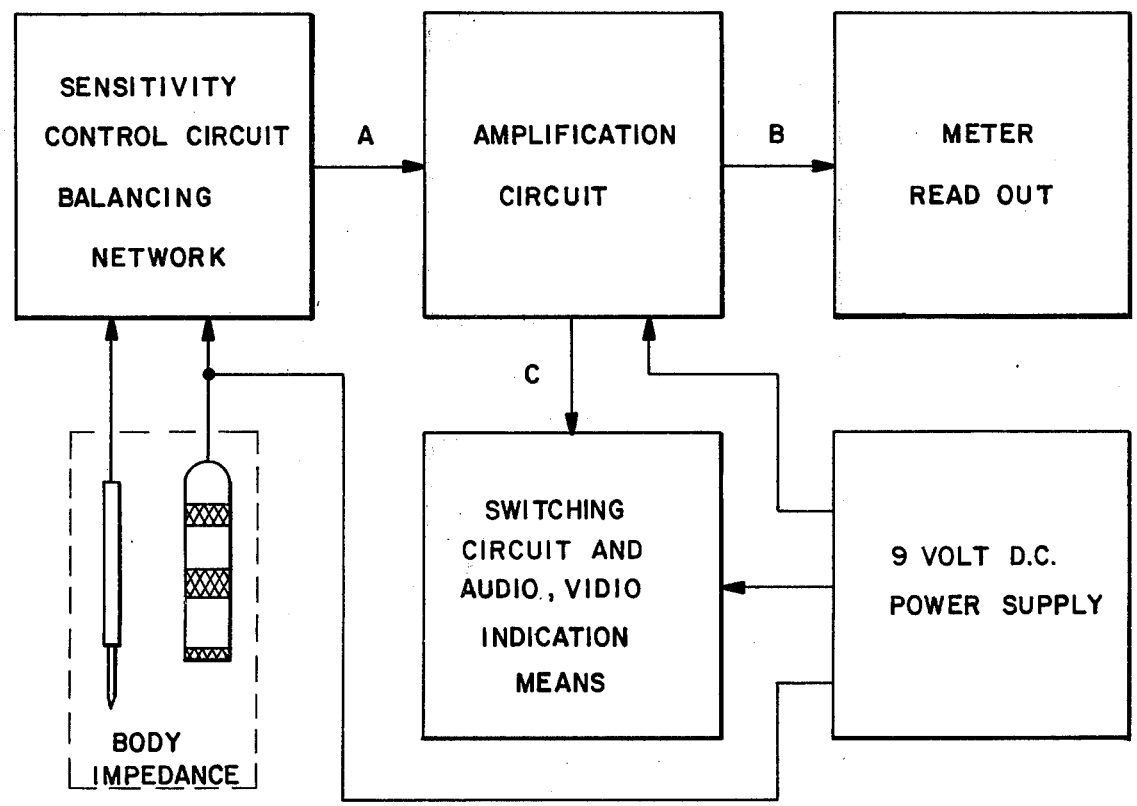
FIG.—2

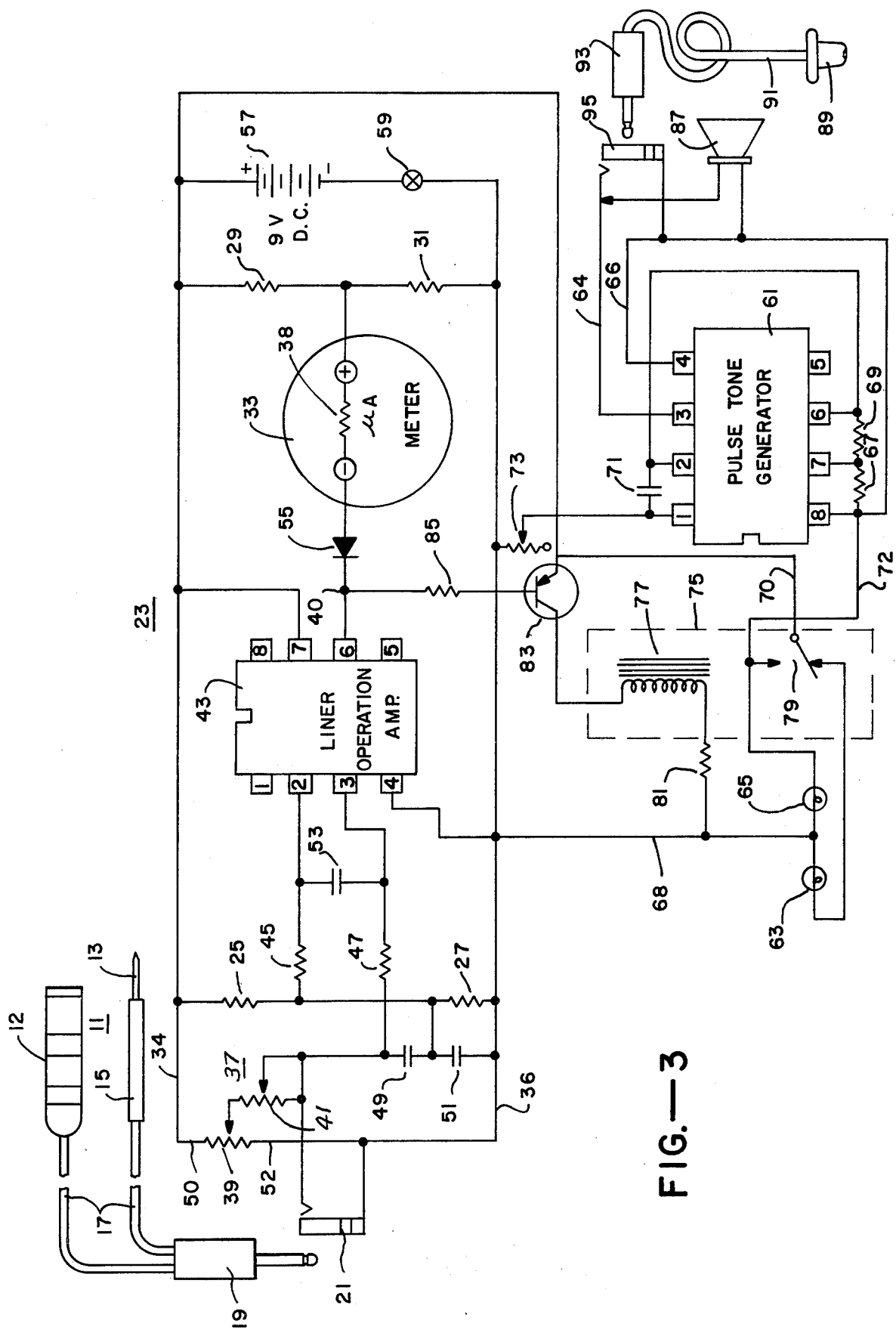
FIG.—3

ELECTRONIC ACUPUNCTURE POINT FINDER

BACKGROUND OF INVENTION

1. Field of Invention

The present invention relates generally to acupuncture devices and more particularly to an electronic acupuncture point finder for use by a physician to accurately locate the acupuncture points on a patient's body.

2. Background of Invention

The nascent interest by the western medical world in the art of Chinese acupuncture has inspired a variety of electronic devices designed to aid the western physician in the practice of this ancient art. The various electronic devices have been particularly important as research tools for the study of the physiological effects of acupuncture under controlled conditions.

The present invention is an unique electronic device designed to allow the western physician to accurately locate acupuncture points on the patient's body. The body is known to have a large number of acupuncture points, 139 on one ear alone, and an experienced Chinese acupuncturist can locate each with remarkable accuracy. The western physician, however, works from point location charts and, unless he has years and perhaps a lifetime of practice and experience, it is difficult for him to locate the points with precision.

It is known that acupuncture points coincidence with points of low body impedance. Electronic devices have been developed to locate these points, however, the problem with these devices is that they are not accurate nor are they reliable in that spurious low impedance areas of the skin can be confused with acupuncture points. Generally, existing devices consist of an oscillator tuned according to the impedance presented to the point finder probe; as the probe is passed over an acupuncture point the pitch of an audio indicator increases. The audio indicator always sounds and the operator must determine which pitch changes correspond to acupuncture points and which are simply spurious or residual in nature, and in addition he must also determine the height of the pitch change for accurately locating the point.

The present invention overcomes the above-mentioned problems by providing an electronic acupuncture point finder which operates in an on/off mode only giving a positive indication only when the point finder electrode touches an acupuncture point, and wherein spurious changes of body impedances are not indicated. Because of the on/off operation of the present invention, acupuncture points can be easily and accurately located by the physician.

Another disadvantage with existing point finder devices is that they have been known to shock or otherwise cause patient discomfort. The present invention overcomes this problem by providing an acupuncture point finder which can operate on a single 9 volt d.c. battery. Indeed, the present invention is of a compact, lightweight, and low power design which provides portability and ease of operation in addition to this overall safety consideration.

SUMMARY OF INVENTION

The present invention is an electronic acupuncture point finder comprised of a point finder probe and a grabber electrode formed to be secured to or held by the patient. The point finder probe includes an insulated handle portion and a point finder electrode for passing over a patient's skin. A balancing network is electrically connected to the point finder and grabber electrodes and has fixed impedance elements disposed such that the body impedance presented between the points of the body contacted by the point finder electrode and the grabber electrode is compared with the impedance of the fixed impedance elements. An imbalance signal is produced by the balancing network when an impedance different from the nominal body impedance is presented to the point finder electrode being passed over the patient's skin. Means is provided for detecting this imbalance signal and a voltage supply means is provided for driving the balancing network.

OBJECTS OF THE INVENTION

It is therefore an object of the present invention to provide an electronic acupuncture point finder wherein the body's acupuncture points can be located with a high degree of accuracy and reliability.

It is another object of the present invention to provide an electronic acpuncture point finder wherein the detection means is operated in an on/off mode only whereby variations of a continuous reading do not have to be interpreted.

It is a further object of the present invention to provide an electronic acupunture device which will not detect spurious variations in body impedance when the point finder electrode is passed over the patient's skin.

It is still another object of the present invention to provide an electronic acupuncture point finder which does not cause discomfort to the patient.

It is still a further object of the present invention to provide an electronic acupuncture point finder which is operated by a low d.c. power supply and preferrably by a 9 volt dry cell battery.

It is yet another object of the present invention to provide an electronic acupuncture point finder which is lightweight in design and convenient to operate.

Other objects of the present invention will become apparent from the following description of the preferred embodiment.

DESCRIPTION OF THE DRAWINGS

FIG. 1 is a front elevational view of the present invention showing the control panel of the electronic acupuncture point finder.

FIG. 2 is a block diagram of the electrical circuit of the present invention.

FIG. 3 is a schematic diagram of the electrical circuit of the present invention.

DESCRIPTION OF THE PREFERRED EMBODIMENT

Referring now to the drawings, FIG. 3 shows the electrical circuit in schematic form of the preferred embodiment of the present invention. Point finder probe 11 shown in the upper left corner of the figure is comprised of a point finder electrode 13 and insulated handle portion 15. The handle portion of the probe is gripped by the physician who operates the invention by passing the point of the electrode lightly over the patient's skin. A second electrode, grabber electrode 12, is also provided. This electrode is preferably formed to be held in the hand of the patient, however, it is understood that it also could be formed to be secured to or otherwise contact the patient's body so as to complete an electrical circuit therethrough. The body impedance presented between electrodes 12 and 13 will depend on the placement of point finder electrode 13 on the patient's body; as the point finder electrode is passed over the patient's skin, the detected body impedance will usually vary somewhat around a nominal magnitude with substantial variations sometimes occurring under certain skin moisture conditions. The greatest variations in body impedance, however, will be detected when the point finder electrode contacts a body acupuncture point.

Electrodes 12 and 13 are connected to plug 19 through insulated wires 17; plug 19 is removably insertable into jack 21 such that looking from jack 21 one sees the body impedance between the points of the body contacted by electrodes 12 and 13.

Balancing network 23 is connected to output jack 21 through wires 34, 36, and has fixed impedance elements disposed for comparison with the body impedance seen at jack 21 such that a change in the body impedance at the point finder electrode when it is passed over the patient's skin will cause an imbalance between impedances, that is, an imbalance in the balancing network. The fixed impedance elements of the balancing network essentially include resistors 25, 27, 29, 31 and the internal resistance 38 of microammeter 33. Resistors 25, 27 preferably have values of 6.8K ohms and resistors 29, 31, 4.7K ohms. This balancing network together with the body impedance can actually be viewed as a modified wheatstone bridge wherein, as the body impedance presented to jack 21 changes from its nominal value, the imbalance in the circuit will appear as an imbalance signal across resistance 38. Means for detecting this imbalance circuit include microammeter 33, and in addition audio and visual detection means wired from the negative side of the microammeter at 40. The audio and visual detection means are described more fully hereinbelow.

A voltage supply means 57 is provided and preferably consists of a 9 volt battery which is connected in parallel to balancing network 23; the voltage supply means is activated by switch 59.

Amplifier circuit 43 is wired between the left hand elements of the balancing network and the imbalance signal detection means. Preferably the amplifier circuit consists of a commercially available integrated circuit linear operational amplifier, for example, an HEP C6052P having eight leads as shown in FIG. 3. Lead 2 of the amplifier 43 is connected to balancing resistors 25 and 27 through 1K surge resistor 45, and lead 3 of amplifier 43 is wired to one side of output jack 21 through 1K surge resistor 47; these two leads are in turn tied together by 0.01uf spark killer capacitor 53. Two additional 0.01uf spark killer capacitors 49, 51 are provided as shown on the input side of the amplifier circuit. The amplifier circuit is powered by voltage supply means 57 by connecting the voltage supply means to terminals 4 and 7 as shown. The amplifier circuit functions to both amplify the imbalance signal to a level suitable for driving the detection circuits and to provide bistable on/off operation as hereinafter described.

Circuit means is provided for adjusting the sensitivity of the balancing network with respect to changes in the body impedance presented to jack 21 such that a detectable output from amplifier circuit 43 will only be generated when the magnitude of a body impedance change exceeds a certain threshold level. Specifically, the sensitivity adjustment means is comprised of a two pot resistor 37 having a 0-1K trimmer resistor 39 and a 0-1M variable resistor 41. Generally, the 0-1K trimmer resistor is set by the manufacturer whereas the 0-1M variable resistor will be externally adjustable by the operator of the invention. The two main leads 50 and 52 of pot resistor 37 are connected through wires 34, 36 to voltage supply means 57; the center tap leads 54 are connected through wire 38 and surge resistor 47 to terminal 3 of amplifier circuit 43. It can be seen that the voltage division is such that the voltage at terminal 3 of the amplifier circuit can be adjusted relative to the voltage at terminal 2 by adjustment of pot resistor 37 and that the terminal 3 voltage will also be affected by the body impedance presented at jack 21 in that a decrease in body impedance will be accompanied by a decrease in voltage at this terminal. The commercial dual linear operational amplifier 43 is chosen such that it will only amplify a signal at terminal 3 if it is of a voltage smaller than the voltage at terminal 2. Thus, by adjusting pot resistor 37, the voltage terminal 3 of the amplifier circuit can be adjusted sufficiently above the voltage at terminal 2 such that only a desired threshold change in the magnitude of the body impedance will decrease the voltage at terminal 3 sufficiently to overcome the terminal 2 voltage. Such a threshold change would then effectively "turn on" the amplifier circuit.

The output of amplifier circuit 43, which as stated above is a commercially available integrated circuit, is taken from terminal 6 on the left side of the chip. When in an off position, the output of the amplifier circuit at terminal 6 will register a spurious positive voltage. Diode 55 is connected in series with ammeter 33 for filtering out this spurious signal thereby preventing it from affecting the meter; the meter thus zeros when the amplifier circuit is in the off condition allowing meter movements which occur when electrode 13 passes over an acupuncture point to be more easily detected.

Further means for detecting the imbalance signal generated by contact with an acupuncture point are provided to give the physician a further positive and more easily discernable indication of the acupuncture point's presence. Preferably, both audio and visual indicators are provided together with a circuit means for switching these indicators on when an impedance change of suitable magnitude occurs to indicate the presence of an acupuncture point. It is important to note that the present invention contemplates that these additional indicators like ammeter 33 only operate in an on or off mode whereby the physician does not have to interpret between signals as he does in the existing oscillator type devices.

The circuits for the audio and visual indication means are shown in the lower right hand corner of FIG. 3. The audio indicator is comprised of pulse tone generator 61, again a commercially available integrated circuit, for example, an Archer Type 555. External impedance elements are shown to be wired to the pulse tone generator and these elements include an 18K resistor 67 connected between terminals 7 and 8, a 1K resistor 69 connected between terminals 6 and 7, a 0.1uf capacitor connected between terminals 1 and 2 and a 0-3K tone control pot 73 connected between terminal 1 and the negative side of voltage supply means 57. By adjusting the tone control pot, the physician can select a suitable frequency for audio indication.

The output of the pulse tone generator taken from terminals 3 and 4 is connected through wire 64, 66 to speaker 87. An earphone 89 is also provided as an alternative to the speaker output; earphone plug 93, connected by insulated wire 91 to earphone 89, removeably engages earphone jack 95 which is wired in parallel to speaker 87. It is understood that the speaker can be made to disengage from the output circuit when the earphone plug is inserted into earphone jack.

The visual indicators are comprised of two lights 63, 65 of different colors disposed such that the illumination of one color indicates the presence of an acupuncture point and the illumination of the other color indicates the absence of a acupuncture point. Indicating light 63, preferably red in color, is connected to voltage supply means 57 through wires 68 and 70 and also through switch 79 of relay 75. With the relay switch 79 in the open position shown, light 63 is illuminated because of the completed circuit with voltage supply means 57. Light 65, which is preferrably green in color, is similarly wired to voltage means 57 except that it is instead wired to the opposite pole of relay switch 79 whereby with the relay switch in the open position shown the light is not illuminated since its circuit is open. When coil 77 of relay 75 is energized, relay switch 79 closes the circuit of light 65 and correspondingly opens the circuit to light 63.

It is also noted at this point that the switching of relay 75 which closes the circuit to light 65 also activates the pulse tone generator 61 by connecting the voltage supply means to the pulse tone generators terminal 8 through wire 72. With the relay switch in its normally open position, this circuit is open thereby removing the voltage supply means from the pulse tone generator. Therefore, it can be seen that when the relay 75 in its normally open position, red light 63 is illuminated, green light 65 is not illuminated, and the pulse tone generator 61 is inoperative. However, when coil 77 is energized and relay 75 switched to an on or closed position, green light 65 and the pulse tone generator 61 are switched to an on condition and red light 63 is simultaneously switched to an off condition.

The switching circuit means which operates the pulse tone generator and the indicating lights in accordance with the presence or absence of an acupuncture point is comprised of an PNP transistor 83, the base of which is connected to the output of the operational amplifier 43 through 1K resistor 85. The collector of transistor 83 is in turn connected to the positive side of voltage supply means 57, and the emmitter is connected to one end of relay coil 77. The opposite end of the relay coil is wired to the negative terminal of the voltage supply means through 100 ohm resistor 81 which is provided as a current limiting resistor to protect relay 75, preferrably a 6 volt d.c. relay. The switching circuit operates as follows: In absence of a signal at the output of the dual linear operational amplifier 43, that is at terminal 6 as shown in the drawings, transistor 83 is non-conductive and therefore no current flows through coil 77. In the absence of such a current flow, relay switch 79 is in the normally off position as shown. When the change in body impedance is sufficient to turn on amplifier circuit 43, the imbalance signal which appears at terminal 6 turns transistor 83 on which in turn closes the circuit to the voltage supply means causing current to flow through relay coil 77. This in turn causes relay switch 79 to switch to the closed position thereby activating both green light 65 and the pulse tone generator 61 and simultaneously extinguishing red light 63. To the physician operating the acupuncture point finder, the sound generated by speaker 87, or earphone 89, and the illumination of green light 65 will indicate that point finder electrode 13 has passed over a point of sufficiently low body impedance to indicate the presence of a body acupuncture point. If the body impedance change is not sufficient, that is if there is only a spurious change of smaller magnitude, the voltage at terminal 3 of the linear operational amplifier 43 will not be sufficient to turn the amplifier on and thus produce an output at terminal 6. Hence, under these conditions neither the pulse tone generator or green light will be activated.

The overall operation of the circuit above described is best illustrated in the block diagram of FIG. 2 of the drawings. Essentially the body impedance as presented to the point finder and grabber electrodes is presented to the balancing network and sensitivity control circuit. This portion of the overall circuit determines whether there is a change from the nominal body impedance of a patient of suitable magnitude to indicate the presence of a acupuncture point, and upon determining that there is a sufficient change generates an imbalance signal A which is amplified by the amplification circuit. The amplified imbalanced signal B and C are fed respectively to a meter read out and, by way of the switching circuit, to the audio and video indication means. A single 9 volt DC power supply, typically an ordinary dry cell flashlight battery, powers the entire circuit of the electronic acupuncture point finder essentially as shown.

The control panel of the invention is shown in FIG. 1 and comprises all adjustment and indication means in a convenient, easy to operate location. As shown, the control panel comprises probe jack 21 for releasably engaging the point finder probe and grabber electrode which can be conveniently stored in a compartment, not shown, in the back of case 101. Earphone jack 95 is for engaging earphone 89 which likewise can be stored at the rear of the point finder case. Speaker 87 is suitably located as shown, however, it is understood that the location of the speaker is a matter of convenience in that it might also be placed on the top, sides or even the rear of the case. Meter 33 is disposed as shown for easy viewing and located below the meter are indication lights 63 and 65 which also can be easily monitored by the physician. The power switch and sensitivity control means are combined for convenience into knob 97. Finally, tone control knob 103 is provided for adjusting the frequency of the pulse tone generator of the audio indicator.

To operate the electronic acupuncture point finder of the present invention, the physician first engages point finder probe 15 and grabber electrode 12 by inserting plug 19 into probe jack 21; if the physician wishes to use the earphone, the earphone can be simply engaged by inserting plug 93 into earphone jack 95. The device is switched on by turning knob 97 in a clockwise direction. Knob 97 is then set at some arbitrary sensitivity value.

At this point the physician directs the patient to hold grabber electrode 12 in either hand; then by holding insulated portion 15 of point finder probe 11, the physician can pass the electrode 13 of the point finder probe lightly over the patient's skin in an area known to have one or more acupuncture points. Normally the green light 63 will be illuminated; however, when the point finder electrode passes over an acupuncture point green light 63 will go off and red light 65 will come on, and simultaneously a tone will be sounded through speaker 87. If upon passing the point finder electrode over the patient's skin it is difficult to achieve an indication in an area where an acupuncture point is known to exist, the sensitivity of the device can be increased by further turning knob 97 in a clockwise direction. On the other hand, if the tone and green light 65 tend to go on and off eradically and too frequently, then this indicates that the sensitivity has been set too high and that knob 97 should be adjusted in a counter clockwise direction. If the tone from the speaker is displeasing or not particularly audible at the set frequency, then this tone can be adjusted by turning knob 103. When the sensitivity of the acupuncture finder is properly set, the physician can locate an acupuncture point by noting the position of the tip of the point finder electrode when he hears a tone or sees the green light 65 come on and the red light 63 go off. In this manner with relatively little practice the acupuncture points of a patient's body can be accurately located.

The present invention provides an electronic acupuncture point finder which is reliable and which as stated accurately locates a patient's acupuncture points. The invention filters out spurious body impedance changes and operates in an on/off mode thereby eliminating the need for the operator to interpret pitch changes and intensities as is common with existing devices. The present invention has the additional advantage of being a low powered device which will not cause discomfort to the patient and which is relatively compact for portability and convenience of operation.

Though the present invention has been described above in considerable detail, it is not intended that it be limited to such detail, except as may be necessitated by the appended claims.

I claim:

1. In an electronic acupuncture point finder having a point finder probe, a grabber electrode, means, such as an audio or visual means, for indicating to an operator a change in body impedance as the point finder probe is passed over the patient's skin, and a voltage supply means, the improvement comprising
    a balancing network including at least two pairs of fixed impedance elements connected across said voltage supply means for effecting a voltage division between each of said pair of impedance elements,
    a selective amplifier circuit connected across said balancing network between each pair of fixed impedance elements thereof, said selective amplifier circuit having at least two inputs and means for comparing the electrical signals to said two inputs and selectively producing an amplifier signal only when the difference between said inputs are of a preselected value, and
    a sensitivity adjustment circuit electrically interconnecting said point finder probe and grabber electrode to one input of said selective amplifier circuit, said sensitivity adjustment circuit having circuit means for adjusting the voltage level to the input of said amplifier circuit to which said sensitivity adjustment circuit is connected for any given body impedance presented between said point finder probe and grabber electrode whereby said amplifier circuit is only turned on for producing an amplified signal when said body impedance is below a preselected value,
    said means for indicating an impedance change to an operator being driven by the amplified signal from said selective amplifier circuit.

2. The electronic acupuncture point finder of claim 1 wherein said amplifier circuit includes a linear operational amplifier.

3. The electronic acupuncture point finder of claim 1 wherein said circuit means for adjusting voltage level to the input of said amplifier circuit includes a two pot resistor in electrical connection with said voltage supply means and disposed to selectively step down the voltage therefrom and to add said stepped down voltage to a voltage of opposite polarity produced across said body impedance whereby the summation of said stepped down voltage and body impedance voltage is fed to said amplifier circuit input connected to said sensitivity adjustment circuit.

4. The electronic acupuncture point finder of claim 1 wherein said voltage supply means includes a d.c. voltage.

* * * * *